United States Patent
Lafleur et al.

(10) Patent No.: US 10,161,606 B2
(45) Date of Patent: Dec. 25, 2018

(54) LIGHTING DEVICE AND METHOD OF USING THE SAME

(71) Applicant: D-MEDTECH INC., Rosemère (CA)

(72) Inventors: André Lafleur, Boucherville (CA); Hugo Diec, Longueuil (CA); Suzanne Francoeur, Longueuil (CA)

(*) Notice: Subject to any disclaimer, the term of this patent is extended or adjusted under 35 U.S.C. 154(b) by 0 days.

(21) Appl. No.: 15/323,096

(22) PCT Filed: Jul. 22, 2015

(86) PCT No.: PCT/CA2015/050685
§ 371 (c)(1),
(2) Date: Dec. 29, 2016

(87) PCT Pub. No.: WO2016/011553
PCT Pub. Date: Jan. 28, 2016

(65) Prior Publication Data
US 2017/0130942 A1 May 11, 2017

Related U.S. Application Data (60) Provisional application No. 62/027,763, filed on Jul. 22, 2014.

(51) Int. Cl.
*F21L 4/04* (2006.01)
*F21V 21/08* (2006.01)
(Continued)

(52) U.S. Cl.
CPC .......... *F21V 21/0808* (2013.01); *A61B 90/35* (2016.02); *F21L 4/00* (2013.01);
(Continued)

(58) Field of Classification Search
CPC .......... A61B 2017/00862; A61B 2017/00951; A61B 2090/309; A61B 90/90; F21L 4/00;
(Continued)

(56) References Cited

U.S. PATENT DOCUMENTS

| | | | |
|---|---|---|---|
| 2,467,954 A | 4/1949 | Becker | |
| 3,731,084 A * | 5/1973 | Trevorrow | ............ F16M 13/04 362/108 |

(Continued)

FOREIGN PATENT DOCUMENTS

| | | |
|---|---|---|
| EP | 2742910 | 6/2014 |
| JP | 2009297185 | 12/2009 |

OTHER PUBLICATIONS

Supplementary European Search Report—EP15824050—EPO Form 1503 03.82 (P04C04)—dated Nov. 8, 2017—4 pages—Vida, Gyorgy.
(Continued)

*Primary Examiner* — Peggy Neils
(74) *Attorney, Agent, or Firm* — Benoit & Cote Inc.; Charles-Andre Caron (57) ABSTRACT

The present document describes a lighting device comprising: a structure comprising a conformable elongated member being adaptable to a shape of an object for securing the lighting device to the object; a light source attached to the structure thereby defining a connection between the light source and the structure; a power source for providing electrical power to the light source; and a skin overmolded onto the structure, the power source, the connection and part of the light source near the connection. There is also described a method for providing lighting in a confined space where a hand-operated tool is used.

17 Claims, 7 Drawing Sheets

(51) Int. Cl.
*F21L 4/00* (2006.01)
*F21V 21/32* (2006.01)
*G02B 23/24* (2006.01)
*A61B 90/35* (2016.01)
*F21V 21/14* (2006.01)
*F21V 23/00* (2015.01)
*F21V 23/04* (2006.01)
*F21Y 115/10* (2016.01)
*A61B 90/30* (2016.01)
*A61B 17/00* (2006.01)

(52) U.S. Cl.
CPC ............ *F21V 21/08* (2013.01); *F21V 21/145* (2013.01); *F21V 21/32* (2013.01); *F21V 23/001* (2013.01); *F21V 23/0421* (2013.01); *G02B 23/2476* (2013.01); *A61B 2017/00862* (2013.01); *A61B 2017/00951* (2013.01); *A61B 2090/309* (2016.02); *F21Y 2115/10* (2016.08)

(58) Field of Classification Search
CPC .... F21V 21/0808; F21V 21/145; F21V 21/32; F21V 23/0421; F21Y 2115/10; G02B 23/2476
See application file for complete search history.

(56) References Cited

U.S. PATENT DOCUMENTS

| | | | |
|---|---|---|---|
| 5,276,596 A | 1/1994 | Krenzel | |
| 5,385,500 A * | 1/1995 | Schmidt | A63H 3/006 362/189 |
| 5,517,392 A * | 5/1996 | Rousso | F16M 11/40 362/194 |
| 5,921,654 A | 7/1999 | Coyle | |
| 5,944,407 A * | 8/1999 | Lynch | F21L 4/06 362/184 |
| 6,000,809 A * | 12/1999 | Belo | B43K 29/10 362/118 |
| 6,280,050 B1 * | 8/2001 | Bird | F21V 21/32 362/191 |
| 6,379,296 B1 | 4/2002 | Bagget | |
| 6,585,727 B1 | 7/2003 | Cashman et al. | |
| 8,162,517 B2 | 4/2012 | Lee | |
| 8,251,536 B2 * | 8/2012 | Bevirt | F16M 11/40 362/187 |
| 8,556,484 B2 * | 10/2013 | Ho | B60Q 1/26 362/551 |
| 8,789,988 B2 * | 7/2014 | Goldwater | F21S 4/22 362/217.01 |
| 2006/0291195 A1 | 12/2006 | Horrell et al. | |
| 2013/0322083 A1 | 12/2013 | Toaspern | |

OTHER PUBLICATIONS

Bovie Medical Corporation Flexible Lights: http://web.archive.org/web/20130510203545/http://www.boviemedical.com/products_aaronlights_flexible.asp.

PCT/International Search Report (ISR)—PCT/CA2015/050685—Form PCT/ISA/210—dated Sep. 22, 2015—3 pages—Garnet, Jeremy.

Communication pursuant to Article 94(3) EPC by Gyory Vida dated Apr. 12, 2018. EPO Form 2001 (5 pages).

* cited by examiner

LIGHTING DEVICE AND METHOD OF USING THE SAME

CROSS-REFERENCE TO RELATED APPLICATIONS

This application claims priority of U.S. provisional patent application No. 62/027,763, filed on Jul. 22, 2014, the specification of which is hereby incorporated by reference.

BACKGROUND (a) Field

The subject matter disclosed generally relates to battery powered lighting devices. More specifically, the subject matter disclosed relates to compact and conformable battery powered lighting devices capable of adopting various shapes in order to orient lighting from the light source in a selected direction.

(b) Related Prior Art

Many types of portable battery powered lighting devices are known in the art, some being usable to assist a worker in performing a task while ambient light does not provide sufficient luminosity over a specific work zone. Some of the lighting devices are provided with attaching means to keep user's hands free, for example, some are attachable to a helmet or headband (i.e., helmet or headband of a fireman, a miner, a doctor, etc.) to follow the direction of sight of the wearer.

In some cases, the working space is very tight and hardly accessible by a light beam emitted from a lighting device at a distance. It may be difficult or impossible to bring the lighting device within the working space and have the light beam appropriately oriented. Such a situation may be experienced for instance by surgeons, performing a surgery in a compact and deep cavity of an animal or human body.

Few devices have been provided in the prior art to help improve lighting in such conditions.

More than often, such lighting devices fail to provide a truly flexible and dependable light source for illuminating different types of deep and restricted locations. For example, some devices are not adapted to attach to other tools or objects to reach different cavities and provide no flexibility for light beam reorientation with respect to the device's body. Some other lighting devices are not attachable and/or comprise parts (i.e., the one or more batteries and/or the light source itself) that may become loose and be lost (about or within the body cavities), and has no provision for adjustment of the light beam orientation.

None of the prior art devices provides, at the same time, easy and conformable wrapping around a medical device, and flexible light beam reorientation by the user without moving the device body or repositioning attachment, without providing parts that can become loose and be lost about or within the body cavities.

There is therefore a need for an improved lighting device that overcomes the drawbacks of the lighting devices of the prior art.

SUMMARY

According to an embodiment, there is provided a lighting device comprising a structure comprising a conformable elongated member; a light source attached to the structure thereby defining a connection between the light source and the structure; a power source for providing electrical power to the light source; and a skin overmolded onto the structure, the power source, the connection and part of the light source near the connection; wherein the conformable elongated member is capable of adopting various shapes in order to orient lighting from the light source in a selected direction.

According to an aspect, the light source comprises a distal end and further wherein the skin is continuous thereby entirely covering the lighting device with the exception of the distal end of the light source.

According to an aspect, the conformable elongated member comprises a distal end and further wherein the connection is between the light source and the conformable elongated member at the distal end of the conformable elongated member.

According to an aspect, the structure further comprises a power source receiving compartment adapted to receive the power source.

According to an aspect, the conformable elongated member comprises a proximal end opposite the distal end and further wherein the power source receiving compartment extends from the proximal end of the conformable elongated member.

According to an aspect, the conformable elongated member comprises an electrical conductor.

According to an aspect, the electrical conductor comprises a single strand conductor.

According to an aspect, the single strand conductor has a gauge value between 10 and 26.

According to an aspect, the single strand conductor has a gauge value of 14.

According to an aspect, the electrical conductor further comprises a multiple strand conductor.

According to an aspect, the multiple strand conductor has a gauge value between 10 and 26.

According to an aspect, the multiple strand conductor has a gauge value of 26.

According to an aspect, the lighting device further comprises an irreversible one-way switch placed on an electrical path between the power source and the light source, wherein a displacement of the irreversible one-way switch from an original position to an irreversible position allows the electrical power to reach the light source.

According to an aspect, the irreversible one-way switch comprises a dome shaped portion capable of adopting a first opened position and a second closed position, where in the first opened position a space is present between the dome shaped portion and the power source thereby resulting in an open circuit and where in the second closed position the electrical power reaches the light source.

According to an aspect, the lighting device further comprises a removable electrical insulator placed on an electrical path between the power source and the light source to prevent temporarily the electrical power from reaching the light source.

According to an aspect, the light source is a LED.

According to an aspect, the LED emits a white light.

According to an aspect, the LED has a color temperature of about 6500 K.

According to an aspect, the skin comprises an adherent material.

According to an aspect, the skin comprises a flexible elastomeric material.

According to an embodiment, there is provided a method for providing lighting in a confined space where a hand-operated object is used, the method comprising: providing a conformable lighting device having a conformable elongated member and a light source at a distal end of the conformable lighting device; wrapping the conformable elongated member around the hand-operated object; and orienting the distal end of the conformable lighting device in a selected direction such that lighting is projected toward the confined space when the hand-operated object is used.

According to an aspect, the wrapping comprises wrapping the conformable elongated member around a handling portion of the hand-operated tool resulting in a wrapping which does not substantially interfere with an intended use of the hand-operated tool.

Features and advantages of the subject matter hereof will become more apparent in light of the following detailed description of selected embodiments, as illustrated in the accompanying figures. As will be realized, the subject matter disclosed and claimed is capable of modifications in various respects, all without departing from the scope of the claims. Accordingly, the drawings and the description are to be regarded as illustrative in nature, and not as restrictive and the full scope of the subject matter is set forth in the claims.

BRIEF DESCRIPTION OF THE DRAWINGS

Further features and advantages of the present disclosure will become apparent from the following detailed description, taken in combination with the appended drawings, in which.

It will be noted that throughout the appended drawings, like features are identified by like reference numerals.

DETAILED DESCRIPTION

In embodiments, there are disclosed lighting devices for securing to medical devices and methods of using the same.

Referring now to the drawings and more particularly to FIGS. 1, 2, 3A and 3B, there is shown a lighting device 10 for securing to a medical device 12. The lighting device 10 includes a structure 14. The structure 14 includes a conformable elongated member 16 which is adaptable to a shape of the medical device 12 for securing the lighting device 10 to the medical device 12. The lighting device 10 further includes a light source 18 which is attached to the structure 14, thereby defining a connection 20 between the light source 18 and the structure 14. The lighting device 10 also includes a power source 22 for providing electrical power to the light source 18 and a skin 24 which is overmolded onto (i.e., directly onto) the structure 14, the power source 22, the connection 20 and part of the light source 18 near the connection 20.

Figure 1:
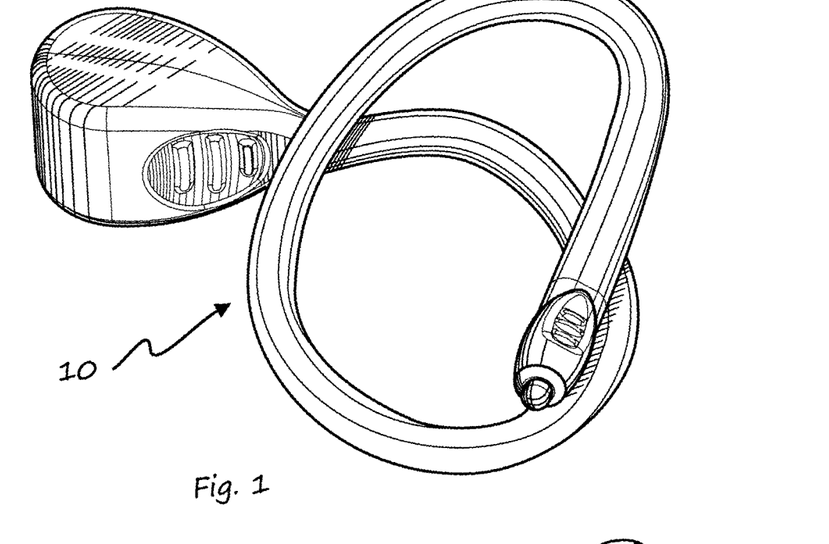
FIG. 1 is a top perspective view of a lighting device in accordance with an embodiment, the lighting device being shown in a standalone fashion.

As shown, thanks to the mechanical properties of its conformable elongated member 16, the lighting device 10 may adopt an infinite range of configurations between its initial (e.g., substantially straight) position (FIG. 3A) and its wrapped position (FIGS. 1 and 2) to adapt itself for attaching to or wrapping around a variety of supporting objects, such as medical devices, for supporting the lighting device 10 and orienting a light beam produced thereby in a desired direction. The lighting device 10 can also be used in a standalone fashion such as shown in FIG. 1.

Figure 2:
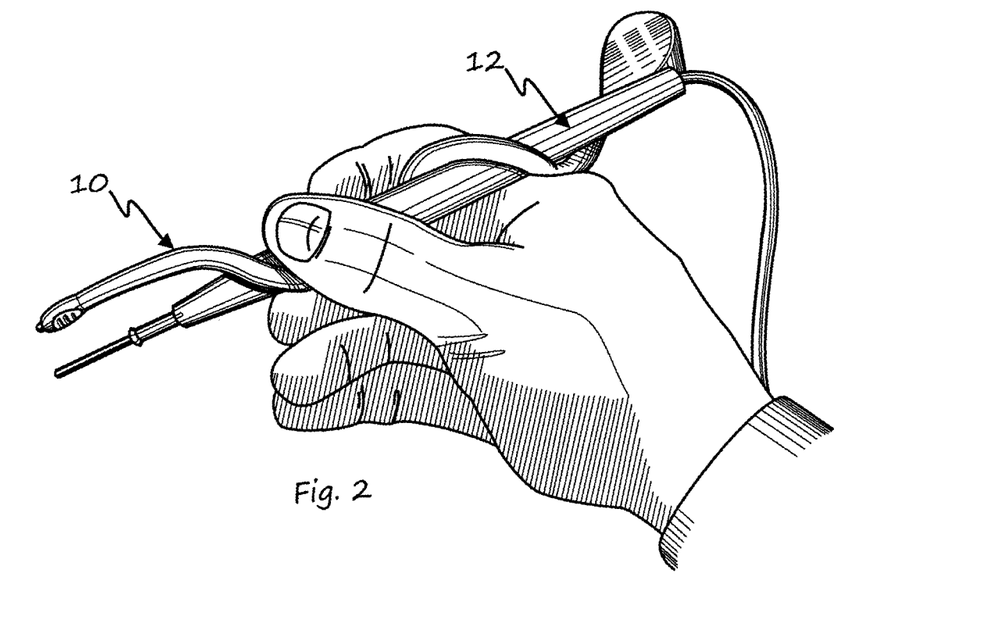
FIG. 2 is a top perspective view of a lighting device in accordance with an embodiment, the lighting device being shown wrapped around a medical device held by a user.

FIG. 2 shows an exemplary use where the lighting device 10 is wrapped around a medical device 12 of a surgery hand tool (i.e., electrocutter) and oriented to provide local lighting in an area in the immediate vicinity of the tool's tip 50 to bring top up light just in a selected work zone.

Still referring to FIGS. 1, 2, 3A and 3B, there is shown that the light source 18 defines a distal end 26 and that the skin 24 is continuous (and gapless), thereby entirely covering the lighting device 10 with the exception of the distal end 26 of the light source 18. It is important to mention that the skin 24 may comprise an adherent material such as to easily wrap around the shape of the medical device 12 for securing the lighting device 10 to the medical device 12. The conformable elongated member 16 defines a distal end 28. The connection 20 is between the light source 18 and the conformable elongated member 16 at distal end 28. The structure 14 further includes a power source receiving compartment 30 which is adapted to receive the power source 22.

According to an embodiment, the light source 18 is permanently connected to the conformable elongated member 16 (i.e., the structure 14), via connection 20, so that there is no chance that the light source 18 falls or is replaced.

The conformable elongated member 16 further defines a proximal end 32 which is opposite the distal end 28. As shown, the power source receiving compartment 30 extends from the proximal end 32 of the conformable elongated member 16.

Figure 6:
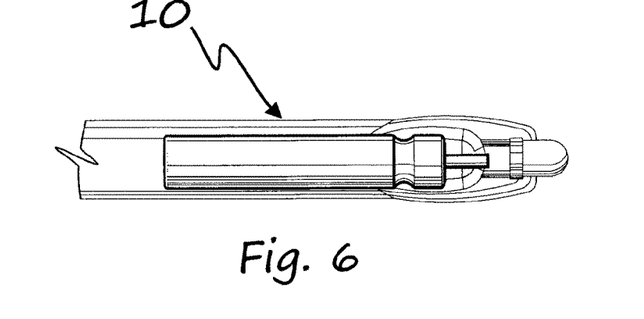
FIG. 6 is a side elevation close up view of light source end of a lighting device according to an embodiment comprising a pin-type battery shown in transparency near the light source (i.e., the distal end)
Figure 7:
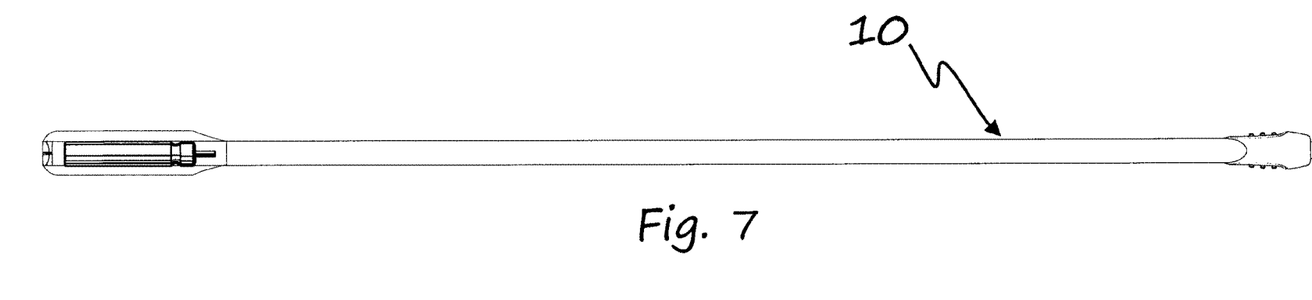
FIG. 7 is a side elevation view of a lighting device according to an embodiment comprising a pin-type battery shown in transparency at the proximal end (i.e., opposite the light source)
Figure 8:
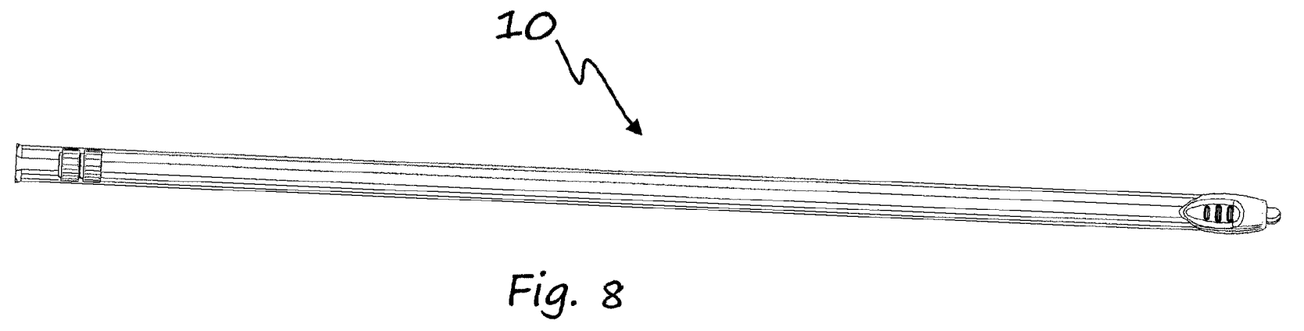
FIG. 8 is a side elevation view of a lighting device according to an embodiment comprising a button-type battery shown in transparency at the proximal end (i.e., opposite the light source)
Figure 9:
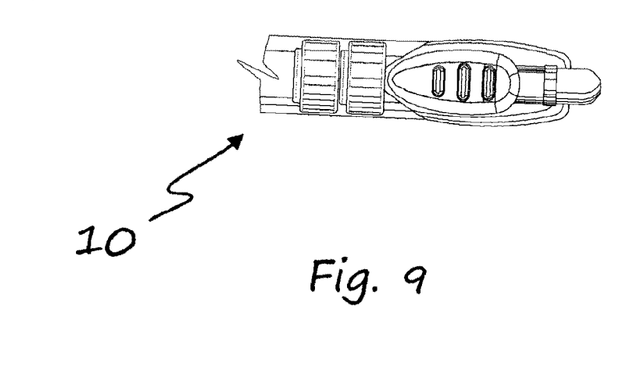
FIG. 9 is a side elevation close up view of light source end of a lighting device according to an embodiment comprising a button-type battery shown in transparency near the light source (i.e., the distal end)
Figure 10:
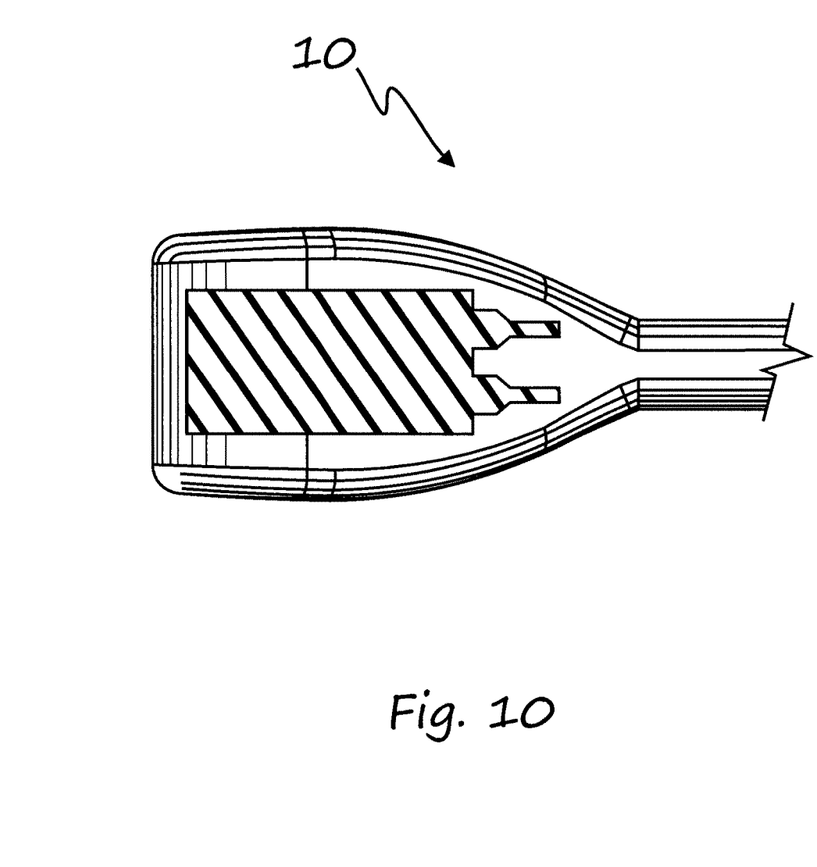
FIG. 10 is a side elevation close up view of a lighting device according to an embodiment comprising a flexible battery shown in transparency at the proximal end (i.e., opposite the light source).

Even if the power source receiving compartment 30 is shown on FIGS. 1, 2, 3A and 3B to be at the extremity of the light source 18 on the structure 14, it is to be mentioned that the power source receiving compartment 30 may be positioned at any distance from the light source 18 of the structure 14. For example, according to another embodiment, it would be possible to have the power source receiving compartment 30 adjacent the light source 18 (see, for example, FIG. 6 and FIG. 9).

Still referring to FIGS. 1, 2, 3A and 3B, there is shown that the conformable elongated member 16 includes an electrical conductor. The electrical conductor includes a first single strand conductor 36 and a second multiple strand conductor 38. Both the first single strand conductor 36 and the second multiple brand conductor 38 constitute an electrical path between the power source 22 and the light source 18, thereby allowing the power, from the power source 22, to reach the light source 18. It is to be mentioned that the electrical conductor 34 may, alternatively, include a first single strand conductor and a second single strand conductor (identical or not in gauge to the first single strand conductor), as long as at least one of the two single strand provides conformable properties to the conformable elongated member 16.

According to an embodiment, the single strand conductor may have a AWG (American Wire Gauge) value between 10 and 26. More particularly, the single strand conductor has a AWG value of 14.

According to an embodiment, the multiple strand conductor may have a AWG value between 10 and 26. More particularly, the multiple strand conductor has a AWG value of 26.

Figures 3A, 3B:
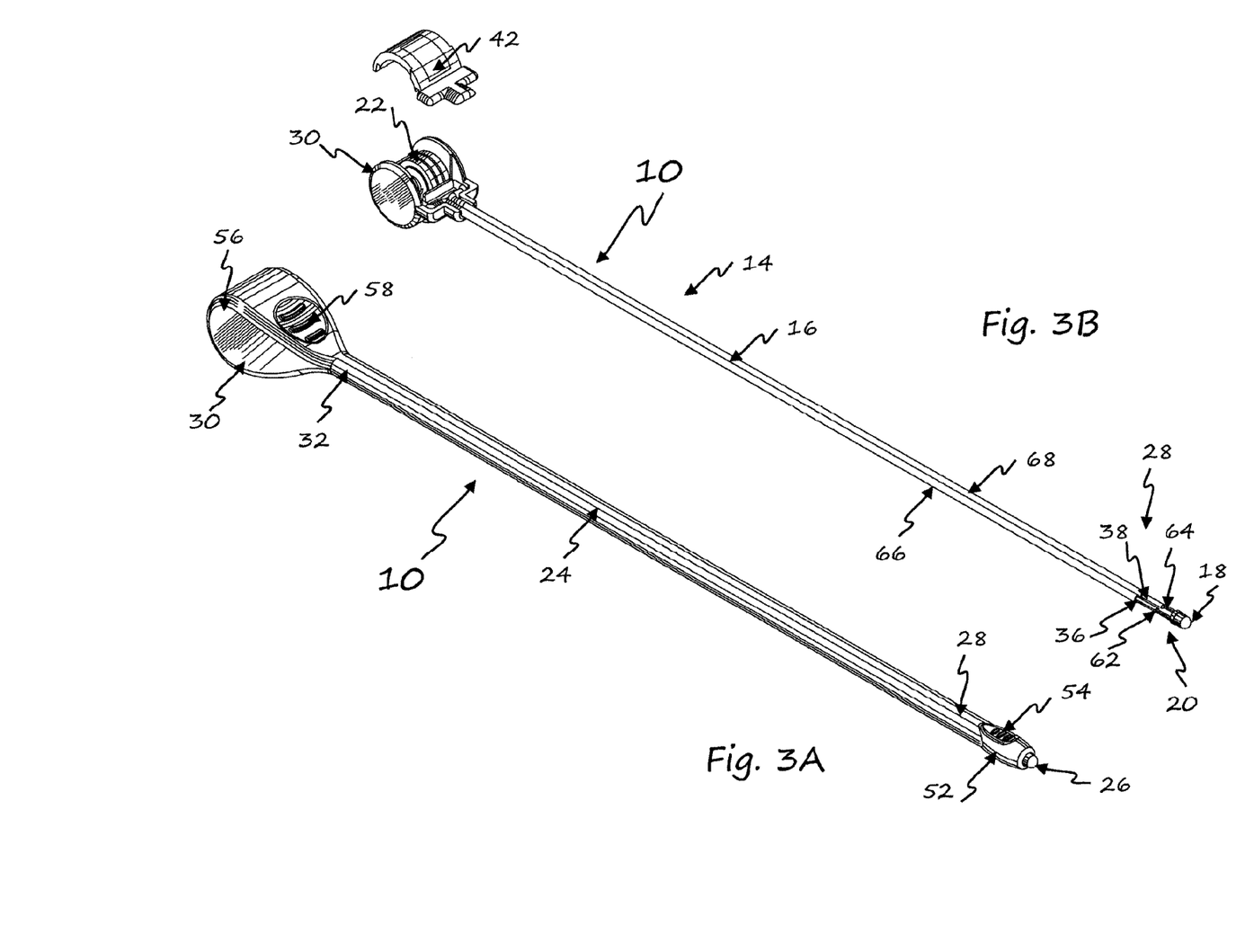
FIG. 3a is a top side isometric view of an embodiment of a lighting device shown in a relaxed attitude.
FIG. 3b is a top side isometric view of the lighting device of FIG. 3a shown prior to final assembly and moulding of the outer elastomeric skin layer.

Referring now more specifically to FIG. 3B, the lighting device 10 is shown, prior to installation of the skin 24, with the conformable elongated member 16 in its straight neutral and relaxed attitude or position.

The total length of the structure 14 may be typically between about 15 and about 30 cm long, which is sufficient to properly attach the lighting device 10 around a wide range of medical devices or any other suitable objects.

As mentioned above, the skin 24 is overmolded onto the power source 22, the connection 20 and part of the light source 18 near the connection 20, such as to allow only a portion of the light source 18 to be uncovered by the skin 24.

As best shown in FIG. 3A, the skin 24 defines a skin head 52 covering part of the light source 18. The skin head 52 includes projections, such as molded ridges 54, to facilitate gripping to fold the conformable elongated member 16 to impose a deformation and configuration for attaching, or wrapping, the lighting device 10 or orienting a light beam emitted from the light source 18 in a desired user defined direction. For example, a user may grip the skin head 52 to fold the distal end 28 to impart a deformation (i.e., reversible permanent deformation) defining a new light beam orientation being passively maintained after the grip is released.

Referring now to FIG. 3A, there is shown that the skin 24 defines a skin tail 56 covering the totality of the power source receiving compartment 30 and the power source 22 itself. Similarly to the skin head 52, the skin tail 56 includes projections or molded ridges 58 to help manipulate the lighting device 10 especially when it becomes soiled with slippery fluids or matters, such as, without limitation, oil, blood, water, and the like.

To complement the attachment flexibility of the lighting device 10, the skin tail 56 covering the power source receiving compartment 30 may further include magnetic members, adhesive members and/or hook and loop members for attachment and/or wrapping purposes against the medical device 12. For example a magnetic attachment element 42 may be mounted inside the structure 14 and underneath skin 24.

The skin 24 may be made of a flexible elastomeric material applied for covering the structure 14, the power source 22, the connection 20 and part of the light source 18, near the connection 20, by a molding process, such as injection over-molding or by dipping. As mentioned above, the skin 24 may further include an adherent material, thereby allowing the skin 24 to adequately wrap around the medical device 12 without slipping.

The desirable Shore-A hardness of the material of the skin 24 may range between about 45 and about 85, and more preferably between about 65 and about 75.

Appropriate materials of the skin 24 may include, without limitation, TPR (thermoplastic resilient), TPE, silicone, polyurethane, nitrile, any other suitable polymeric material, and any combination thereof. More preferably, in medical applications, the material may be hypoallergenic and approved for surgical uses.

Referring now to FIG. 3B, there is shown in more detail the internal components of the lighting device 10 as it is assembled prior to application of the skin 24. A high intensity light emitting diode (LED) forms the light source 18 and comprises the LED chip per se embedded in an optical plastic package defining a converging lens to shape the emitted light beam as a generally conical solid shape projecting about 90% of the light power in a disc of approximately 12 cm in diameter at a distance of 20 cm (17° dispersion with respect to the optical centerline @ 50% intensity, sharply decreasing with increasing angle). The light beam emitted by the selected light source 18 has an intensity of 5100 millicandela (mcd) for a power of 66 milliwatts at a rated supply voltage of 3.3 VDC (20 mA). With two common thin alkaline button electrochemical cells 60a, 60b (see FIG. 4E) typically providing 90 to 110 mAh @ 3.0 VDC, the working life expectancy of the lighting device 10 may then easily exceed one hour. It is to be mentioned that the power source receiving compartment 30 may receive one, two or more cells, such as cells 60a, 60b (see FIG. 4E), to operate the light source 18. The power source, operation voltage, amperage, light output power and color may vary according to the availability or specification change of any of these components.

Still referring to FIG. 3B, there is shown that the connection 20 between the light source 18 and the structure 14 includes a pair of electrical terminals 62, 64 which emerge from the light source 18 and which electrically connect to the electrical conductor (i.e., the first single strand conductor 36 and the second multiple strand conductor 38). An insulating sheath must cover at least one of the strand conductors 36, 38 to provide electrical isolation between each other. In the embodiment shown in FIG. 3B, single strand conductor 36 has an insulation sheath layer 66 and multiple strand conductor 38 has an insulating sheath layer 68.

An aspect of the lighting device 10 is that the mechanical properties of the conformable elongated member 16 that make it compliant and subject to reversible permanent deformation to enable wrapping around an object to support the lighting device 10, solely relies on the mechanical properties of the electrical conductor 34 (i.e., on the mechanical properties of at least one of first single strand conductor 36 and second multiple strand conductor 38). Indeed, although a small electrical current is drawn from the cells 60a, 60b (see FIG. 4E) to the light source 18 or LED, at least one of the first single strand conductor 36 and second multiple strand conductor 38 is selected in a larger gauge to benefit from the rigidity and formability of the electrical conductor, a copper conductor for instance.

Therefore, one 14 AWG strand conductor (1.6 mm diameter) may be used with a stranded 26 (0.4 mm diameter) AWG strand conductor. Alternatively, a pair of 16 AWG solid strand conductors may be used for similar performance regarding the formability of the conformable elongated member 16. Obviously, different combinations may be selected to provide the desired compliance and formability, and according to the attachment strength required to properly hold a lighting device 10 of a given weight.

It is to be mentioned that the elastomeric continuous skin 24 coating the structure 14, the power source 22, the connection 20 and part of the light source 18 near the connection 20 provides a flexible, reliable and cost effective means for attaching the compact lighting device 10 to provide user orientable top up lighting for a wide of applications, especially in work sites with restricted areas or cavities, such as in medical applications.

Referring now to FIGS. 4A to 4E there is shown that the lighting device 10 may alternatively include a removable electrical insulator 48, which is placed on the electrical path between the power source 22 and the light source 18 such as to prevent temporarily the electrical power from reaching the light source 18. Once the removable electrical insulator 48 is removed from between the power source 22 and the light source 18, the electrical power may reach the light source such as to operate the lighting device 10.

Figure 4A:
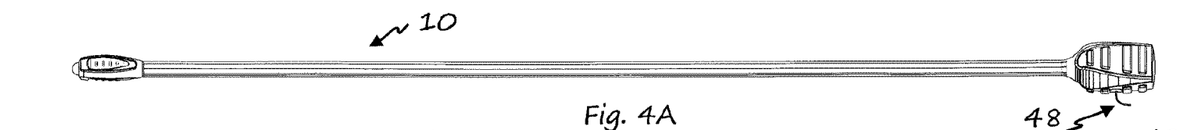
FIG. 4A is a side elevation view of a lighting device according to an embodiment comprising a removable electrical insulator.
Figures 4B, 4C, 4D, 4E:
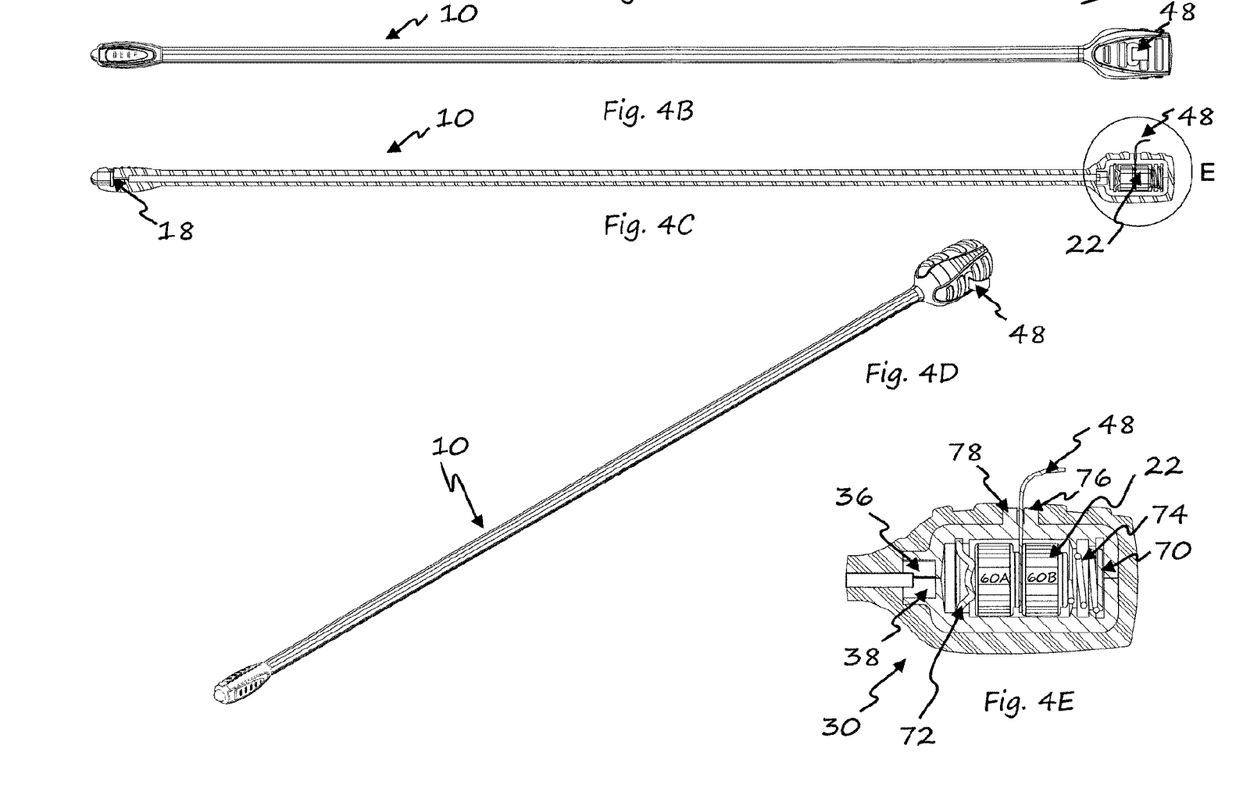
FIG. 4B is a bottom plan view of the lighting device of FIG. 4A.
FIG. 4C is a side cut out view of the lighting device of FIG. 4A.
FIG. 4D is a top side isometric view of the lighting device of FIG. 4A.
FIG. 4E is a close-up side cut out view of the battery compartment section of the lighting device of FIG. 4A.
Figure 5A:
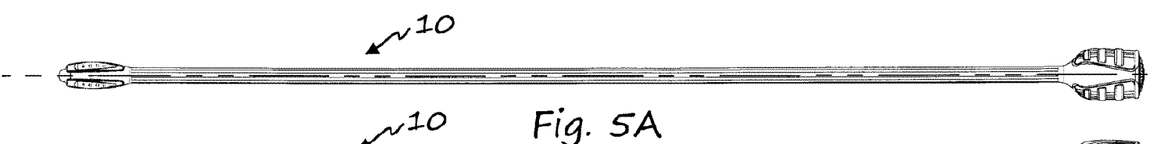
FIG. 5A is a side elevation view of a lighting device according to an embodiment comprising an irreversible one-way switch.
Figures 5B, 5C, 5D, 5E:
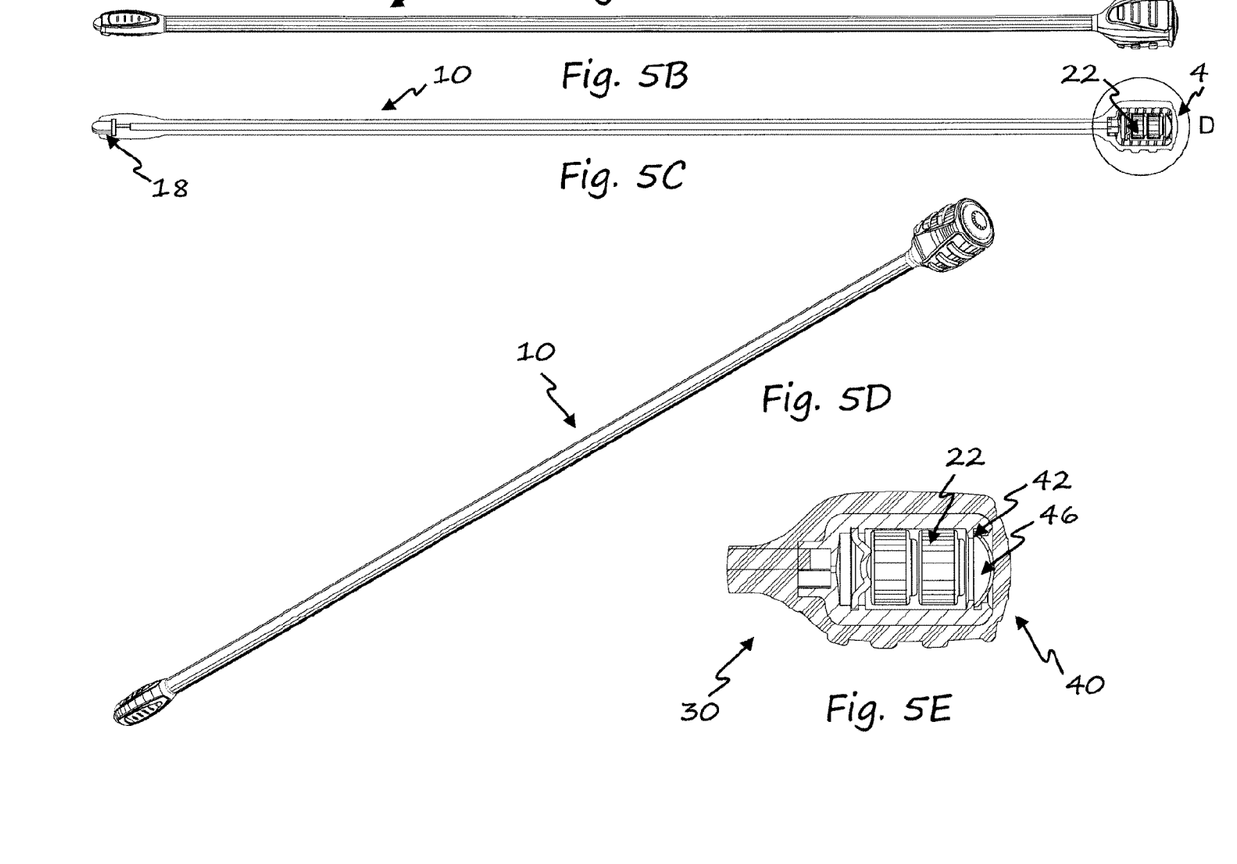
FIG. 5B is a bottom plan view of the lighting device of FIG. 5A.
FIG. 5C is a side cut out view of the lighting device of FIG. 5A.
FIG. 5D is a top side isometric view of the lighting device of FIG. 5A.
FIG. 5E is a close-up side cut out view of the battery compartment section of the lighting device of FIG. 5A.

As best seen from FIG. 4E, an electrically conductive compression spring 74 is assembled to electrode plate 70 and two 1.5 VDC button electrochemical cells 60a, 60b are mounted in electrical series under compression between the electrically conductive compression spring 74 and the electrode plate 72. Thereby, electrical power may be drawn from the cells 60a, 60b to supply a nominal voltage of 3.0 VDC to the light source 18 or LED through single and multiple strand conductors 36, 38.

It is to be mentioned that alkaline cells may be preferred for a disposable lighting device for environmental considerations. According to the embodiment shown in FIGS. 4A to 4E, in a way to prevent electrical power from flowing through the light source 18 or LED before lighting is required, the removable electrical insulator 48 is inserted between the two cells 60a, 60b (or between two adjacent cells from a plurality of cells in the case where there are more than two cells).

Referring now to the embodiment of FIGS. 4A to 4E, there is shown that a slot 76 is provided in the skin 24 (covering the power source receiving compartment 30) to access the power source receiving compartment 30. The slot 76 is provided with a peripheral lip 78. Skin 24 is applied over the structure 14, the power source 22, the connection 20 and part of the light source 18 around the peripheral lip 78, leaving the slot 76 clear to access the inside of power source receiving compartment 30, just between and at the interface of the cells 60a, 60b. Thereby, the removable electrical insulator 48 may be place in the slot 76 during assembly to prevent cells 60a, 60b from contacting each other and thereby prevent electrical current from flowing to energize light source 18 or LED. Once remove, the removable electrical insulator 48 cannot be reinserted in the slot 76.

According to the embodiment shown in FIGS. 4A to 4E, when a user wants to power the lighting device 10, he merely has to pull out the removable electrical insulator 48, providing the lighting device 10 to be a single use lighting device 10, as pulling out the removable electrical insulator 48 from the slot 76 irreversibly powers the light source 18 (until cells 60a, 60b stops to provide power after a certain amount of time). Therefore, the lighting device 10 may be built as a single use lighting device 10 that would remain lit from the time the removable electrical insulator 48 is pulled by a user to the time cells 60a, 60b have their energy completely spent through the light source 18 or LED.

Building the lighting device 10 as a single use device is desirable in the context of medical or surgery use to avoid such issues as detachable parts (with the exception of the removable electrical insulator 48 that needs to be removed from slot 76) and need for sterilization between uses.

Therefore, in a typical embodiment, the lighting device 10 has no moving part except the removable electrical insulator 48 (of the embodiment shown in FIGS. 5A to 5E), is sold in a sterile package and is disposable. After opening the package and pulling the removable electrical insulator 48 (or positioning the dome shaped portion 44 in the second closed position, according to the embodiment shown in FIGS. 5A to 5E), the lighting device 10 may remain lit for use for about half an hour to about two hours and can be eliminated as other medical supplies or recycled after a single use. Thereby, manufacturing cost as well as manipulation and risks are reduced to a strict minimum.

According to another embodiment, and referring now to FIGS. 5A to 5E, there is shown that the lighting device 10 further includes an irreversible one-way switch 40. The irreversible one-way switch 40 is placed on the electrical path between the power source 22 and the light source 18. The activation of the irreversible one-way switch 40 allows the electrical power to reach the light source. The irreversible one-way switch 40 includes a dome shaped portion 44 which is capable of adopting a first opened position and a second closed position (not shown). In the first opened position, a space 46 is present between the dome shaped portion 44 and the power source 22, thereby resulting in an open circuit. On the other hand, in the second closed position, dome shaped portion 44 pushes on the power source 22 and the electrical power reaches the light source 18.

According to an embodiment, the light source 18 of the lighting device 10 described above is a LED (Light Emitting Diode).

According to an embodiment, the power source comprises one or more commercially available batteries. Some examples of models of such batteries include: LR41 alcaline manganese, LR1120 Silver oxide, BR425 LITHIUM 3V 425 (PIN) by Panasonic®, BR435 LITHIUM 3V 435 (PIN) by Panasonic®, BR322: 3 V 20 mAh 22.5×3 mm, BR316: 3V 13 mAh 16×3 mm, BR327 lithium 3v 425 (PIN) with color LED, R435, JR435, 377-376 Silver Oxide by Energizer®, AC230 Zinc-air by Energizer®, CR1025 manganese by Energizer®, CR11632 lithium, CR1620 3v 140 mAh 16 mm×2 mm, BR1225 3v 48 mAh 12 mm×2.5 mm, Flexible rechargeable 3.7v li-po 451268, Flexible rechargeable 3.7v li-po 351672, Flexible rechargeable 3.7v li-po 401230, Flexible rechargeable 3.7v li-po 201021, sheet batteries, ultra thin batteries, flexible batteries, Blue spark 110-ST1 1.5 V 30 mAh 55×47×0.75 mm, CP0452345 Li-po 3.0 V 30 mAh 0.45×23×45 mm, and CR66500 Li-po 3.0V 250 mAh 6.8 diam×51 mm.

The light spectrum emitted by the light source 18 or LED is selected to generally match that of a surgery room light, to provide proper color rendering; e.g., of body tissues in a cavity of an animal or human body. Accordingly, a white light may be considered appropriate. More particularly, a white light with a color temperature of between about 4000K and 7500K may be considered appropriate. Even more particularly, a white light with a color temperature of about 6500K may be considered appropriate.

It is to be mentioned that, although the lighting device 10 is shown and described as referring to applications in the field of medical surgery, it should be deemed usable in a variety of applications requiring an attachable source of local top up lighting.

It is also to be mentioned that, although the lighting device 10 is shown and described as being for a "single-use", it is possible that in other embodiments a two-way switch would be provided.

While preferred embodiments have been described above and illustrated in the accompanying drawings, it will be evident to those skilled in the art that modifications may be made without departing from this disclosure. Such modifications are considered as possible variants comprised in the scope of the disclosure.

The invention claimed is:

1. A lighting device to be operated in combination with a hand-operated tool or a medical device, comprising:
   a structure comprising a conformable elongated member adapted to wrap around the hand-operated tool or medical tool;
   a light source attached to the structure thereby defining a connection between the light source and the structure;
   a power source for providing electrical power to the light source; and
   a skin, distinct from the structure and overmolded onto:
      the structure;
      the power source;
      the connection; and
      part of the light source near the connection,
   wherein the skin comprises an adherent material such that when the conformable elongated member is wrapped around the hand-operated tool or medical tool, the lighting device is secured to the hand-operated tool or medical tool;
   wherein the conformable elongated member is capable of adopting various shapes in order to orient lighting from the light source in a selected direction.

2. The lighting device of claim 1, wherein the light source comprises a distal end and further wherein the skin is continuous thereby entirely covering the lighting device with the exception of the distal end of the light source.

3. The lighting device of claim 1, wherein the conformable elongated member comprises a distal end and further wherein the connection is between the light source and the conformable elongated member at the distal end of the conformable elongated member.

4. The lighting device of any one of claim 1, wherein the structure further comprises a power source receiving compartment adapted to receive the power source.

5. The lighting device of claim 3, wherein the conformable elongated member comprises a proximal end opposite the distal end and further wherein the power source receiving compartment extends from the proximal end of the conformable elongated member.

6. The lighting device of any one of claim 1, wherein the conformable elongated member comprises an electrical conductor.

7. The lighting device of claim 6, wherein the electrical conductor comprises a single strand conductor.

8. The lighting device of claim 7, wherein the single strand conductor has a gauge value between 10 and 26.

9. The lighting device of claim 7, wherein the electrical conductor further comprises a multiple strand conductor.

10. The lighting device of claim 9, wherein the multiple strand conductor has a gauge value between 10 and 26.

11. The lighting device of any one of claim 1, further comprising an irreversible one-way switch placed on an electrical path between the power source and the light source, wherein a displacement of the irreversible one-way switch from an original position to an irreversible position allows the electrical power to reach the light source.

12. The lighting device of claim 1, wherein the skin comprises a flexible elastomeric material.

13. A method for providing lighting in a confined space where a hand-operated tool or a medical device is used, the method comprising:
   providing a conformable lighting device having a conformable elongated member and a light source at a distal end of the conformable lighting device;
   overmolding a skin, distinct from the conformable elongated member and comprising an adherent material, onto:
      the conformable elongated member; and
      part of the light source near the connection;
   wrapping the conformable elongated member around a handling portion of the hand-operated tool or medical tool, thereby having the adherent material securing the conformable lighting device to the hand-operated tool or medical device; and
   orienting the distal end of the conformable lighting device in a selected direction such that lighting is projected toward the confined space when the hand-operated tool or medical device is used.

14. The method of claim 13, wherein the wrapping around the handling portion of the hand-operated tool or medical device results in a wrapping which does not substantially interfere with an intended use of the hand-operated tool or medical tool.

15. The lighting device of claim 1, wherein the skin material has a Shore-A hardness ranging between 45 and 85.

16. The lighting device of claim 1, wherein the skin material has a Shore-A hardness ranging between 65 and 75.

17. The lighting device of claim 1, wherein the skin material consists in one of TPR (thermoplastic resilient), TPE, silicone, polyurethane, nitrile and a polymeric material.

\* \* \* \* \*